United States Patent
Erdemir et al.

(10) Patent No.: US 10,973,768 B2
(45) Date of Patent: Apr. 13, 2021

(54) EXTENDED RELEASE PHARMACEUTICAL FORMULATIONS OF WATER-SOLUBLE ACTIVE PHARMACEUTICAL INGREDIENTS AND METHODS FOR MAKING THE SAME

(71) Applicant: Bristol-Myers Squibb Company, Princeton, NJ (US)

(72) Inventors: Deniz Erdemir, Princeton, NJ (US); Shih-Ying Chang, Princeton, NJ (US); Divyakant Desai, Princeton, NJ (US); San Kiang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 702 days.

(21) Appl. No.: 14/381,944

(22) PCT Filed: Feb. 28, 2013

(86) PCT No.: PCT/US2013/028289
§ 371 (c)(1),
(2) Date: Aug. 28, 2014

(87) PCT Pub. No.: WO2013/130785
PCT Pub. Date: Sep. 6, 2013

(65) Prior Publication Data
US 2015/0050335 A1    Feb. 19, 2015

Related U.S. Application Data

(60) Provisional application No. 61/605,622, filed on Mar. 1, 2012, provisional application No. 61/608,152, filed on Mar. 8, 2012.

(51) Int. Cl.
| | |
|---|---|
| *A61K 9/48* | (2006.01) |
| *A61K 9/28* | (2006.01) |
| *A61K 9/16* | (2006.01) |
| *A61K 9/14* | (2006.01) |
| *A61K 31/155* | (2006.01) |
| *A61K 9/24* | (2006.01) |
| *A61J 3/10* | (2006.01) |
| *A61K 9/20* | (2006.01) |
| *A61K 31/7004* | (2006.01) |
| *A61K 31/403* | (2006.01) |

(52) U.S. Cl.
CPC ............... *A61K 9/2054* (2013.01); *A61J 3/10* (2013.01); *A61K 9/146* (2013.01); *A61K 9/1682* (2013.01); *A61K 9/209* (2013.01); *A61K 9/2086* (2013.01); *A61K 9/2095* (2013.01); *A61K 9/28* (2013.01); *A61K 9/4833* (2013.01); *A61K 9/4866* (2013.01); *A61K 31/155* (2013.01); *A61K 31/403* (2013.01); *A61K 31/7004* (2013.01); *A61K 9/1694* (2013.01)

(58) Field of Classification Search
None
See application file for complete search history.

(56) References Cited

U.S. PATENT DOCUMENTS

| | | | |
|---|---|---|---|
| 2,991,226 A | 7/1961 | Millar et al. | |
| 5,877,224 A | 3/1999 | Brocchini et al. | |
| 6,706,283 B1 | 3/2004 | Appel et al. | |
| 6,933,380 B2 * | 8/2005 | Huang | C08B 37/003 424/457 |
| 7,951,400 B2 | 5/2011 | Desai et al. | |
| 9,248,139 B2 * | 2/2016 | Chang | A61K 9/14 |
| 2006/0083784 A1 | 4/2006 | Ignatious et al. | |
| 2010/0074950 A1 | 3/2010 | Sesha | |
| 2011/0028456 A1 | 2/2011 | Lulla et al. | |
| 2012/0282336 A1 * | 11/2012 | Abebe | A61K 31/7034 424/465 |

(Continued)

FOREIGN PATENT DOCUMENTS

| | | |
|---|---|---|
| EP | 0807433 | 11/1997 |
| WO | 20111060256 | 5/2011 |

OTHER PUBLICATIONS

Erdennir et al. (Org. Process Res. Dev. 2018, 1383-1392).*

(Continued)

*Primary Examiner* — Patricia Duffy
*Assistant Examiner* — Garen Gotfredson
(74) *Attorney, Agent, or Firm* — Mcdonnell Roohnpn Hulbert & Bergholf LLP (57) ABSTRACT

The present disclosure relates to methods for making extended-release formulations of water-soluble active pharmaceutical ingredients such as metformin HCl. In one aspect, the disclosure provides a method that includes adding an aqueous solution of an active pharmaceutical ingredient to an agitated mixture of one or more release-modifying polymers and optionally one or more binders in one or more organic solvents, the one or more organic solvents together being an antisolvent for the active pharmaceutical ingredient, water being sufficiently soluble in the one or more organic solvents such that the water added as part of the aqueous solution dissolves in the mixture, the addition thereby precipitating the active pharmaceutical ingredient; separating the active pharmaceutical ingredient and the one or more release-modifying polymers and, if present, the one or more binders from the one or more organic solvents to yield co-processed particles; and drying the co-processed particles. The methods can be used to make dosage forms such as tablets having reduced amounts of release-modifying polymers.

29 Claims, 6 Drawing Sheets

(56) References Cited

U.S. PATENT DOCUMENTS

2016/0102093 A1* 4/2016 Chang .................. A61K 9/14
544/337

OTHER PUBLICATIONS

International Search Report of Published International Application WO2013130785 published Sep. 6, 2013.
International Preliminary Report on Patentability dated Sep. 2, 2014 of International Patent Application No. PCT/US2013/028289 filed Feb. 28, 2013.

* cited by examiner

Dissolve metformin in 2.8 vol water

Add in 2 hours ↓

20% wt HPMC K100
+ 5% wt NaCMC
Slurried in 15.6 vol acetone
+ 11.8 vol ethyl acetate

FIG. 1

Filter slurry & deliquor (not completely)

↓

Displacement wash with 6 vol acetone/water
(4.5-7.5% water)

↓

Reslurry wash with 6 vol acetone/water
(4.5-7.5% water)

↓

Continuous agitation without vacuum and heat

↓

Periodic agitation with vacuum at 60°C

Raman images of physical blend of metformin and HPMC-K100M

Raman images of physical blend of co-processed material

EXTENDED RELEASE PHARMACEUTICAL FORMULATIONS OF WATER-SOLUBLE ACTIVE PHARMACEUTICAL INGREDIENTS AND METHODS FOR MAKING THE SAME

CROSS-REFERENCE TO RELATED APPLICATIONS

This application is a U.S. national stage application of International Patent Application no. PCT/US2013/028289, filed Feb. 28, 2013, which claims the benefit of priority to U.S. Provisional Patent Application Ser. No. 61/605,622, filed Mar. 1, 2012, and to U.S. Provisional Patent Application Ser. No. 61/608,152, filed Mar. 8, 2012, each of which is hereby incorporated herein by reference in its entirety.

BACKGROUND OF THE DISCLOSURE

1. Field of the Disclosure

The present disclosure relates generally to pharmaceutical compositions and methods for making them. More particularly, the present disclosure relates to methods for making extended-release formulations of water-soluble active pharmaceutical ingredients such as metformin HCl.

2. Technical Background

Metformin is an antihyperglycemic agent of the biguanide class used in the treatment of non-insulin dependent diabetes mellitus. It is usually marketed in the form of its hydrochloride salt under the trade name GLUCOPHAGE® and GLUCOPHAGE® XR.

Metformin hydrochloride has intrinsically poor permeability in the lower portion of the gastrointestinal tract, leading to absorption almost exclusively in the upper part of the gastrointestinal tract. Its oral bioavailability is in the range of 40 to 60%, decreasing with increasing dosage, which suggests some kind of saturable absorption process, or permeability/transit time limited absorption. It also has a very high water solubility (>300 mg/mL at 25° C.). This can lead to difficulty in providing a slow release rate from a formulation and problems in controlling the initial burst of drug from such a formulation. These two difficulties are further compounded by the high unit dose, typically 500 mg, 750 mg or even 1000 mg, usually required for metformin hydrochloride.

Drugs that have absorption limited to the upper gastrointestinal tract coupled with poor absorption in the distal small intestine, large intestine and colon are conventionally regarded as inappropriate candidates for formulation into oral controlled delivery systems. This limitation on absorption (for example, in the upper gastrointestinal tract) is referred to as the "absorption window."

The gastrointestinal tract functions to propel ingested material from the stomach (where digestion takes place) into the small intestine (where absorption principally occurs) and on to the large intestine (where water is absorbed/secreted as part of body fluid regulation processes). Residence time for non-digestible materials in the stomach depends on whether one is dealing with a fed or a fasted subject. Typical gastric emptying times for particulate material (greater than a few millimeters in diameter) vary from a few tens of minutes in the fasted state to a few hours in the fed state. Transit times through the small intestine are consistently on the order of 3 to 4 hours.

Oral controlled release delivery systems function by releasing their payload of drug over an extended period of time following administration. Thus, controlled release dosage forms may only spend a relatively short period in the regions of the gastrointestinal tract where good absorption of certain drugs can occur. The dosage form will pass on to regions of the intestine where absorption of certain drugs is poor or non-existent, still releasing its contained drug albeit with a significant percentage of its payload still to be delivered. Drug when released from the dosage form in the circumstances described will not be absorbed. Thus, administration of a drug subject to a window of absorption in a conventional controlled release delivery system can lead to subtherapeutic blood levels and ineffective treatment of the disease state for which the drug was intended.

Drugs with very high solubility in water (for example, greater than 100 mg/mL) can be difficult to formulate into a controlled release oral dosage form. Solubility is a driving force for a drug substance to dissolve in water; the greater the solubility the greater the rate of dissolution when all other factors are maintained constant.

In a controlled release dosage form, the formulator tries to reduce the rate of dissolution by, for example, embedding the drug in a polymeric matrix or surrounding it with a polymeric barrier membrane through which drug must diffuse to be released for absorption. To reduce the rate of release of drug from the dosage form to an appropriate level consistent with the blood level profile desired for a drug possessing very high water solubility, very large amounts of polymer would be required for the matrix or barrier membrane. If the total daily dose of drug to be delivered is of the order of only a few milligrams this may be feasible, but many drugs having the solubility properties described require total daily doses of the order of many hundreds of milligrams. Whilst it is possible to create oral controlled release dosage forms for such products by use of large amounts of polymer, an unacceptably large dosage form may result. For example, a 1000 mg metformin HCl tablet made using conventional methods can be so large that it would be difficult for many patients to swallow.

SUMMARY OF THE DISCLOSURE

One aspect of the disclosure is a method for making a pharmaceutical composition including a water-soluble active pharmaceutical ingredient and one or more release-modifying polymers and optionally one or more binders. The method includes adding an aqueous solution of the active pharmaceutical ingredient to an agitated mixture of the one or more release-modifying polymers and optionally the one or more binders in one or more organic solvents, the one or more organic solvents together being an antisolvent for the active pharmaceutical ingredient, water being sufficiently soluble in the one or more organic solvents such that the water added as part of the aqueous solution dissolves in the agitated mixture, the addition thereby precipitating the active pharmaceutical ingredient; separating the active pharmaceutical ingredient and the one or more release-modifying polymers and, if present, the one or more binders from the one or more organic solvents to yield co-processed particles; and drying the co-processed particles.

Another aspect of the disclosure is a pharmaceutical composition made according to the methods described herein.

Another aspect of the disclosure is a pharmaceutical composition including a particulate phase, the particulate phase including a water-soluble active pharmaceutical ingredient in an amount in the range of about 60 wt % to about 95 wt %; and one or more release-modifying polymers and optionally one or more binders in an amount in the range of about 5 wt % to about 40 wt %. The particulate phase can be, for example, a compressed particulate phase, such as a layer of a tablet.

Various embodiments of the disclosure can result in one or more advantages over conventional methods and pharmaceutical compositions. The resulting particulate matter can have excellent flow, and can have a decreased risk of segregation during downstream handling and tabletting. In addition, the intimate mixing of active pharmaceutical ingredient and polymer(s) in certain embodiments can decrease the amount of polymer(s) required to achieve the targeted dissolution profile, leading to reduced tablet mass and size. In certain aspects of the disclosure, the methods can also eliminate the steps of dry powder blending, high shear wet granulation, and drying required in current commercial manufacturing processes.

Various aspects of the disclosure will be further described with reference to embodiments depicted in the appended drawings. It will be appreciated that elements in the figures are illustrated for simplicity and clarity and have not necessarily been drawn to scale. For example, the dimensions of some of the elements in the drawings may be exaggerated relative to other elements to help to improve understanding of embodiments of the disclosure.

BRIEF DESCRIPTION OF THE DRAWINGS

The accompanying drawings are not necessarily to scale, and sizes of various elements can be distorted for clarity.

DETAILED DESCRIPTION

In one aspect, the disclosure provides a method for making an extended-release pharmaceutical composition that includes a water-soluble active pharmaceutical ingredient and one or more release-modifying polymers and optionally one or more binder. The method includes adding an aqueous solution of an active pharmaceutical ingredient to an agitated mixture of the one or more release-modifying polymers and optionally the one or more binders in one or more organic solvents. The one or more organic solvents together are an antisolvent for the active pharmaceutical ingredient, and water is sufficiently soluble in the one or more organic solvents (i.e., together) such that the water added as part of the aqueous solution dissolves in the mixture. Accordingly, the active pharmaceutical ingredient precipitates into the mixture. In certain embodiments, the active pharmaceutical ingredient crystallizes into the mixture. The active pharmaceutical ingredient and the one or more release-modifying polymers and, if present, the one or more binders are then separated from the one or more organic solvents, thereby yielding co-processed particles, which are then dried.

The dried co-processed particles can be further processed in any number of ways. For example, in one embodiment, the dried co-processed particles are compressed, alone or together with other excipients or active pharmaceutical ingredients, to form one or more tablets. Indeed, the co-processed particles according to certain embodiments of the disclosure can be directly compressed, without the need for intermediate steps (e.g., wet or dry granulation, milling). The one or more tablets can be coated or further processed, as would be apparent to the person of skill in the art.

In another embodiment, the dried co-processed particles are filled in one or more capsules, alone or together with other excipients or active pharmaceutical ingredients, to form one or more capsule dosage forms.

In certain particular embodiments, the active ingredient is a metformin salt, such as metformin HCl, metformin succinate or metformin fumarate. Moreover, in view of the present disclosure the person of skill in the art can use other water-soluble active pharmaceutical ingredients in the practice of the methods of the present disclosure, for example by adapting the particular procedures described herein.

In certain embodiments, the method begins with providing an aqueous solution of the active pharmaceutical ingredient, for example by dissolving the active pharmaceutical ingredient in water (or another aqueous solution) to prepare a concentrated solution, e.g., in the range of 50 mg/mL to saturation, in the range of 100 mg/mL to saturation, or even in the range of 200 mg/mL to saturation. In certain embodiments, the aqueous solution is under-saturated, for example, at no more than 99% of saturation, in order to prevent precipitation of the active pharmaceutical ingredient before addition to the mixture. For example, in one embodiment, the aqueous solution of the active pharmaceutical ingredient is metformin HCl at a concentration of about 270 mg/mL (2.8 L aqueous solvent per kg of solid metformin HCl). At this concentration, the metformin HCl solution is under-saturated.

In a separate precipitation vessel, the one or more organic solvents are prepared. As noted above, the one or more organic solvents together are an antisolvent for the active pharmaceutical ingredient. That is, the active pharmaceutical ingredient is substantially insoluble in the one or more organic solvents together (e.g., in certain embodiments, the active pharmaceutical ingredient has a solubility in the mixture of the one or more organic solvents of less than about 10 mg/mL). Moreover, as noted above, water is sufficiently soluble in the one or more organic solvents (i.e., together) such that the water added as part of the aqueous solution dissolves in the mixture. For example, in certain embodiments, the one or more organic solvents together will dissolve at least 10 wt % water, at least 15 wt % water, at least 20 wt % water, or even at least 25 wt % water.

In certain embodiments, the one or more organic solvents include a mixture of acetone and ethyl acetate. For example, in one embodiment, the one or more organic solvents include acetone in the range of 40 vol %-80 vol % and ethyl acetate in the range of 20 vol %-60 vol %. In another embodiment, the one or more organic solvents include acetone in the range of 45 vol %-70 vol % and ethyl acetate in the range of 30 vol %-55 vol %. In certain embodiments, the volume ratio of acetone to ethyl acetate is in the range of 4:6 to 8:2. In other embodiments, the volume ratio of acetone to ethyl acetate is in the range of 45:55 to 70:30. In still other embodiments, the volume ratio of acetone to ethyl acetate is in the range of 50:50 to 64:36. In certain embodiments, the one or more organic solvents include substantially no other solvents. In other embodiments, the one or more organic solvents include one or more additional solvents up to a level of about 10 vol %. In one particular embodiment, the one or more organic solvents are a mixture of acetone (57 vol %) and ethyl acetate (43 vol %). The person of skill in the art will determine other solvents that could be used in practicing the methods of the disclosure. For example, in certain embodiments, solvents such as ethanol, THF, isopropyl acetate and butyl acetate can be used. In one embodiment, the one or more organic solvents includes one or more of acetone, ethanol or THF (e.g., in the range of 40 vol %-80 vol %) in combination with one or more of ethyl acetate, isopropyl acetate and butyl acetate (e.g., in the range of 20 vol %-60 vol %).

In certain embodiments, the volume of the aqueous solution of active pharmaceutical ingredient is substantially less than the volume of the one or more organic solvents. For example, in one embodiment, the ratio of the volume of the aqueous solution of active pharmaceutical ingredient to the volume of the one or more organic solvents is in the range of 1:2 to 1:40. In another embodiment, the ratio of the volume of the aqueous solution of active pharmaceutical ingredient to the volume of the one or more organic solvents is in the range of 1:4 to 1:20. For example, in one particular embodiment, the volume of the one or more organic solvents is 7 times the volume of the aqueous solution of active pharmaceutical ingredient.

As the person of skill in the art will appreciate, a variety of release-modifying polymers can be used as the one or more release-modifying polymers. The one or more release-modifying polymers and the one or more organic solvents can in certain embodiments be selected such that the polymer(s) do not substantially dissolve in the organic solvent(s). In certain such embodiments, the one or more release-modifying polymers include hydroxypropylmethylcellulose (HPMC) (e.g., as at least 50% of the total weight of the one or more release-modifying polymers and the optional one or more binders). For example, in one embodiment, the release modifying polymer is hydroxypropylmethylcellulose (e.g., HPMC K100M). The person of skill in the art will determine other release-modifying polymers that could be used in practicing the methods of the present disclosure.

In certain embodiments, no separate binder is used in the agitated mixture, and no separate binder is included in the pharmaceutical composition. In certain such embodiments, the release-modifying polymer also functions as a binder.

In other embodiments, one or more binders are included in the agitated mixture of polymers. As the person of skill in the art will appreciate, a variety of binders can be used as the one or more binders. The one or more binders and the one or more organic solvents can in certain embodiments be selected such that the polymer(s) do not substantially dissolve in the organic solvent(s). In certain embodiments, the one or more binders include hydroxypropylcellulose, ethyl cellulose or methyl cellulose (e.g., as at least 50% of the total weight of the one or more binders). In certain embodiments, the binder is sodium carboxymethylcellulose (NaCMC). In other embodiments, the binder is hydroxypropylcellulose (HPC), ethyl cellulose or methyl cellulose. The person of skill in the art will determine other binders that could be used in practicing the methods of the present disclosure.

As noted above, the one or more release-modifying polymers and optionally the one or more binders are used in the form of a mixture with the one or more organic solvents. The mixture can be, for example, a suspension or a slurry. In certain embodiments, substantially none of the polymer is dissolved in the one or more organic solvents, and substantially no polymer dissolves in the final solvent mixture after the addition, such that substantially no polymer is lost to the solvent phase in the separation step. For example, in certain embodiments, less than 5%, less than 2%, or even less than 1% of the polymer material dissolves in the final solvent mixture after the addition.

The aqueous solution of the active pharmaceutical agent is added to an agitated mixture of the one or more release-modifying polymers and optionally the one or more binders. The addition can occur at a variety of temperatures, e.g., in the range of 0° C.-30° C. In one particular embodiment, the addition is performed at about 20° C. The agitation can be performed in a variety of manners. For example, a stirrer can be used to agitate the mixture contained in a vessel. In other embodiments, the addition can be performed in a tubular system, for example with venturi mixing to provide the agitation.

In certain embodiments, the addition is performed gradually, such that the precipitated (e.g., crystallized) active pharmaceutical ingredient is evenly distributed among the co-processed particles. For example, the addition can be performed over a time of at least 5 minutes, at least 15 minutes, or even at least an hour. For example, in one particular embodiment, the addition is performed over a time in the range of two to three hours.

Because the active pharmaceutical ingredient is substantially insoluble in the one or more organic solvents, it precipitates (e.g., crystallizes) upon addition. For example, in certain embodiments, at least about 80%, at least about 85%, or even at least about 90% of the active pharmaceutical ingredient precipitates upon addition. The active pharmaceutical ingredient precipitate particles (e.g., crystallites) agglomerate with the one or more release-modifying polymers and, if present, the one or more binders to form particles. In certain embodiments, the one or more solvents includes ethyl acetate. For example, in one embodiment, ethyl acetate is present in the one or more organic solvents in an amount ranging from 20 vol % to 100 vol %, or even in the range of 30 vol % to 55 vol %. As described in more detail below, the present inventors have determined that the use of ethyl acetate can help to agglomerate the particles of the active pharmaceutical ingredient and to swell the polymers to make them agglomerate more strongly with one another and with the particles of active pharmaceutical ingredient to form particles.

After the addition step, the active pharmaceutical ingredient and the one or more release-modifying polymers and, if present, the one or more binders are separated from the one or more organic solvents to yield co-processed particles. A variety of methods can be used to separate the one or more organic solvents from the particles. For example, in certain embodiments, the separation is performed by filtration. In other embodiments, the separation is performed by centrifugation.

In certain embodiments, the co-processed particles are not completely deliquored during the separation, such that they are not completely dried. The present inventors have determined that co-processed agglomerates can form very hard lumps when dried without agitation if the water is not removed efficiently. The filtered particles can be washed with a water-miscible organic solvent (e.g., acetone) to remove some of the water, and to help distribute the remaining water throughout the particles. The water miscible solvent can be a solvent that does not dissolve the one or more release-modifying polymers and, if present, the one or more binders, such that substantially no polymer is lost during the washing. The water miscible solvent is also selected such that it does not substantially dissolve the water-soluble active pharmaceutical ingredient. Agitation can be used to increase the efficiency of the wash. The water miscible solvent can be, for example, acetone. In other embodiments, the water miscible solvent is an alcohol (e.g., ethanol, isopropanol, butanol). The person of skill in the art will select an appropriate water-miscible solvent (e.g., a single solvent or a mixture of solvents) depending on the identities of the active pharmaceutical ingredient and polymer(s) used.

In certain embodiments, it can be desirable to leave some water in the polymer(s); accordingly, the water miscible solvent can include a relatively small amount of water (e.g., in the range of about 1 wt % to about 10 wt %, for example, in the range of about 2 wt % to about 7 wt %).

The co-processed particles can then be dried. Drying can be performed, for example, using vacuum, heat or a combination of the two. Flowing gas can also be used. In other embodiments, the drying can be performed at ambient temperatures and pressures. In certain embodiments, the drying is performed with agitation. The agitation along with any water remaining in the co-processed particles can cause densification of the material during drying. For example, in one drying protocol, the co-processed particles are agitated for a period of time in ambient conditions, then dried under vacuum at elevated temperature (e.g., about 60° C.) with periodic agitation. Of course, in other embodiments, the drying can be performed without agitation (e.g., in a tray).

The co-processed particles can be formed into pharmaceutical dosage forms in a variety of ways, as would be apparent to the person of skill in the art. For example, in one embodiment, the dried co-processed particles are compressed to form a tablet. In certain embodiments, no additional excipients are added to the particles before compression. In other embodiments, other excipients are added to the dried, co-processed particles before compression, for example, in an amount up to 10%, up to 5%, or up to 2%. In certain embodiments, the only additional excipients added are one or more lubricants, glidants or anti-adherents such as magnesium stearate, calcium stearate, stearic acid, oil (e.g., vegetable or mineral), talc or silicon dioxide. The tablet can be coated with one or more coatings, which can contain a variety of additional ingredients, including a second active pharmaceutical ingredient (e.g., saxagliptin or a pharmaceutically acceptable salt thereof). In certain the embodiments, the dried co-processed particles are compressed with a plurality of second particles to form a multilayer tablet (e.g., a bilayer tablet). The second particles can, for example, include a second active pharmaceutical ingredient, for example, dapagliflozin.

In another embodiment, the dried, co-processed particles are filled in one or more capsules to form one or more capsule dosage forms.

Figure 1:
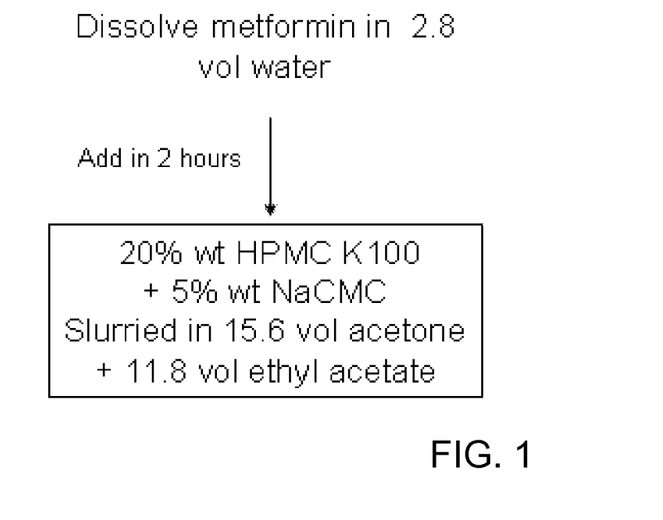
FIG. 1 is a flowchart depicting the crystallization protocol for a metformin HCl formulation according to one embodiment of the disclosure.

One embodiment of the disclosure provides a method for making a pharmaceutical formulation of metformin HCl. First, metformin HCl (which can be commercially obtained) is dissolved in water to form an aqueous solution (~270 mg/mL, 2.8 vol with respect to metformin HCl). At this concentration, the metformin HCl solution is under-saturated. FIG. 1 is a flowchart depicting the addition step for a targeted co-processed product composition of 80 wt % metformin HCl, 16 wt % HPMC K100M and 4 wt % NaCMC. In the flow diagram, the volumes and polymer weight ratios are given with respect to the metformin HCl input to the process. The polymer input to the process is determined based on the amount of metformin HCl that will crystallize at the end of the process, not based on the metformin HCl input. Crystallization yield for metformin HCl at the end of the process is determined as 90% due to the solubility of metformin in the final solvent composition. On the other hand, the solubility of the polymers in the final mother liquor is very low. As a result there is negligible polymer loss during the process. Therefore, the metformin HCl input weight into the process is 4.45 times the total polymer input weight in order to achieve 80% metformin HCl potency in the final product.

To perform the crystallization, an organic solvent mixture of 57 vol % acetone and 43 vol % ethyl acetate is prepared in a separate vessel. The total volume of the mixture of organic solvents is 7 times the volume of the aqueous solution of metformin HCl. The release-modifying polymer HPMC K100M, and optionally the binder sodium carboxymethylcellulose (NaCMC) are suspended in this solvent mixture at 20° C. with vigorous agitation to form a slurry. The aqueous solution of metformin HCl step is then added into the polymer slurry over a time period of 2-3 hours while agitating vigorously. Both acetone and ethyl acetate are anti-solvents for metformin hydrochloride; i.e., solubility of metformin hydrochloride (HCl) is less than 10 mg/mL in both solvents. Therefore, metformin HCl crystallizes when added into the acetone/ethyl acetate mixture. Metformin HCl crystals agglomerate together with the polymer to form particles. The slow addition and vigorous agitation can help to ensure that the metformin hydrochloride is evenly distributed among the polymer particles.

The particles are filtered to form a filter cake, and the cake is then washed with 6 volumes (i.e., 6 L per kg of metformin HCl input) of aqueous acetone (4.5-7.5 wt % water), followed by a re-slurry wash with the same solvent composition. This can remove the excessive amount of water and distributes water evenly in the cake. The cake is then dried, with agitation. The agitation along with the water in the cake can cause densification of the material during drying. For example, when the material is co-processed as described above and dried without agitation, the bulk density of the co-processed particles is typically in the range of 0.16-0.23 g/mL. When the drying is performed with agitation, the bulk density of the co-processed particles is typically in the range of 0.35-0.39 g/mL.

Figure 2:
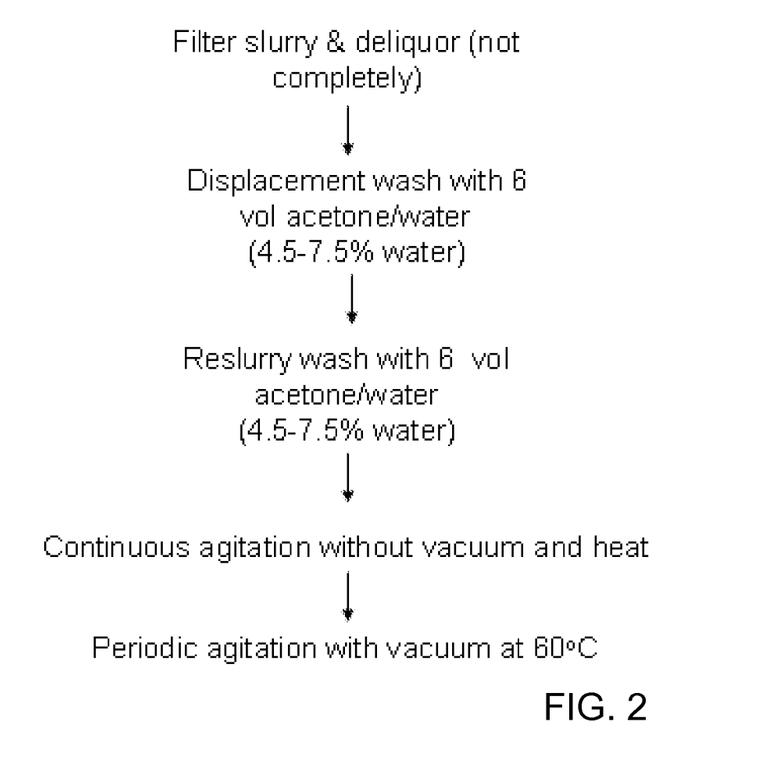
FIG. 2 is a flowchart depicting an isolation procedure for a metformin HCl formulation according to one embodiment of the disclosure.

One embodiment of a filtration and drying protocol is depicted in flowchart form in FIG. 2. Here, the particles are agitated continuously without vacuum and heat, and then dried The HPMC K100M and NaCMC polymers are substantially insoluble in the acetone/ethyl acetate compositions of the crystallization step, and in the acetone/water composition used to wash the co-processed particles, substantially no polymer is lost to the solvent phase in the separation step.

Figure 3:
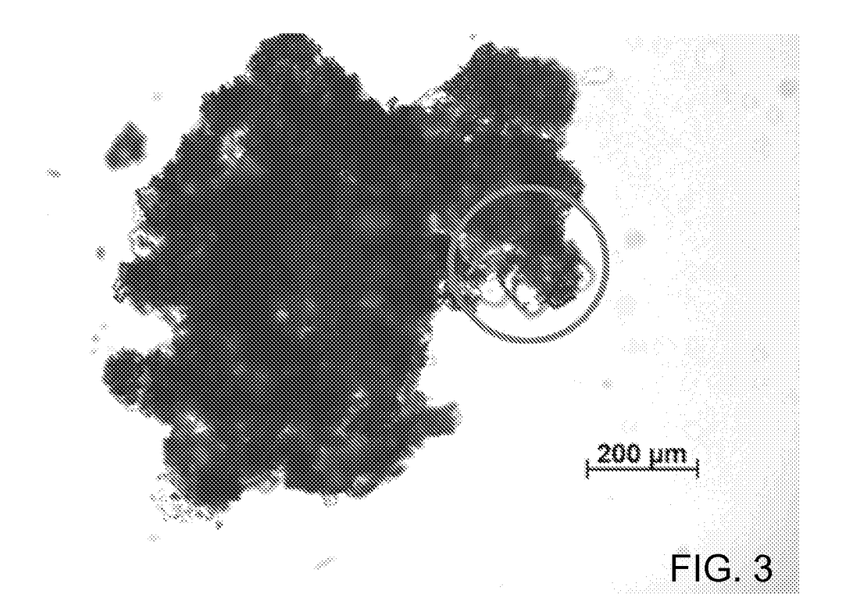
FIG. 3 is a micrograph of an co-processed particle generated in one embodiment of the disclosure.

FIG. 3 is a microscopic image of typical agglomerate generated by the above-described process. The image is taken as the agglomerate is still in the mother liquor, before isolation. The surface of the agglomerate is covered with metformin HCl crystals. The polymer in the agglomerate appears as transparent (circled in FIG. 3) due to the swelling of the polymer by the water.

In certain aspects, the present disclosure provides a method to reduce the polymer content required for extended release, thus allowing a smaller tablet size for an equivalent dose. For example, Table 1 provides a comparison of a tablet formed by the compression of the co-processed metformin HCl particles described above with a current commercial extended release metformin formulation. In the 1000 mg commercial formulation, 27.1 wt % of the tablet is the release modifier polymer HPMC K100M, 3.45 wt % of the tablet is the binder NaCMC, and 69 wt % of the tablet is metformin HCl. This relatively large amount of polymer is required in order to achieve the dissolution profile desired in an extended release formulation. This results in a relatively high tablet weight of 1450 mg. In the formulation made using the co-processed particles described above, HPMC K100M is also used as the release modifier polymer, similar to the current formulation, but with much lower amount of 16%. Accordingly, the tablet formed from the co-processed particles is only 1264 mg in total weight. Optionally, the binder NaCMC can be omitted from the formulation by increasing the release modifier polymer HPMC K100M amount to 20% without changing the total tablet weight.

TABLE 1

| Component | Function | Co-processed Met XR 1000 mg | Metformin XR 1000 (commercial) |
|---|---|---|---|
| Metformin HCl | API | 79.50% | 68.96% |
| Sodium Carboxymethylcellulose | Binder | 4% | 3.45% |
| HPMC-K100M | Release modifier | 16% | 27.1% |
| Syloid 244 | Glidant | — | — |
| Magnesium Stearate | Lubricant | 0.50% | 0.50% |
| Core Tablet Weight | | 1264 mg | 1450 mg |

Figure 4:
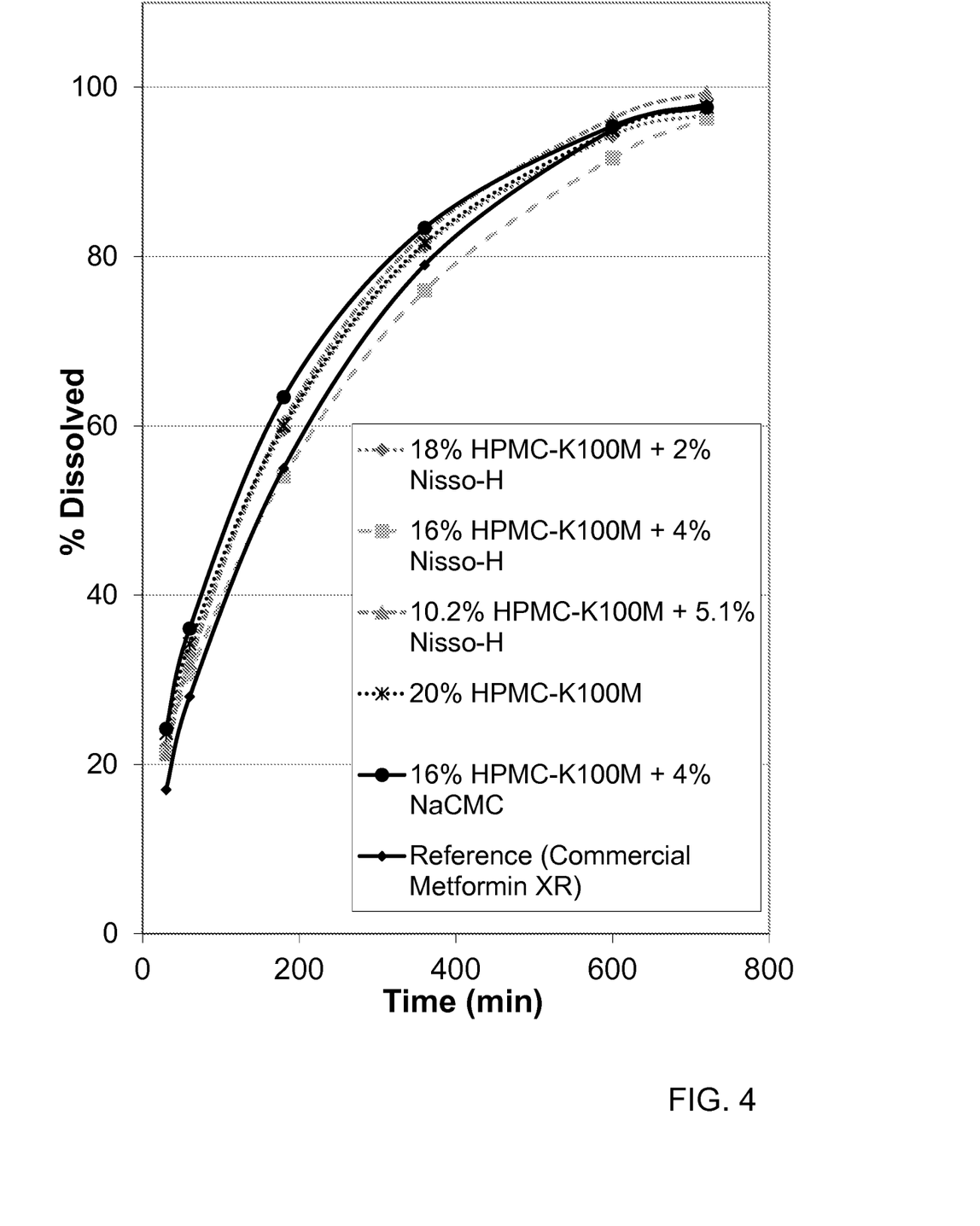
FIG. 4 is a graph of dissolution profiles for a variety of tablets according to various embodiments of the disclosure, as compared to a commercial 1000 mg metformin formulation.

Multiple binders are screened for the use in the formulations of the present disclosure, such as HPC (NissoH), HPC (HXF) and NaCMC. The dissolution profiles of 1000 mg tablets prepared by using different combinations of release modifying polymer optionally with binder in 1000 mL pH 6.8 phosphate buffers are shown in FIG. 4, along with the dissolution profile of current commercial 1000 mg metformin HCl formulation. Even when the release modifier polymer HPMC K100M amount is as low as 10.2%, the dissolution profile remains comparable to the reference profile. As the person of skill in the art would understand from the dissolution profiles, a variety of binders are suitable for use in the formulations of the present disclosure. Similarly, as demonstrated by the fourth entry in the legend, in certain formulations of the present disclosure no binder is necessary.

Figure 5:
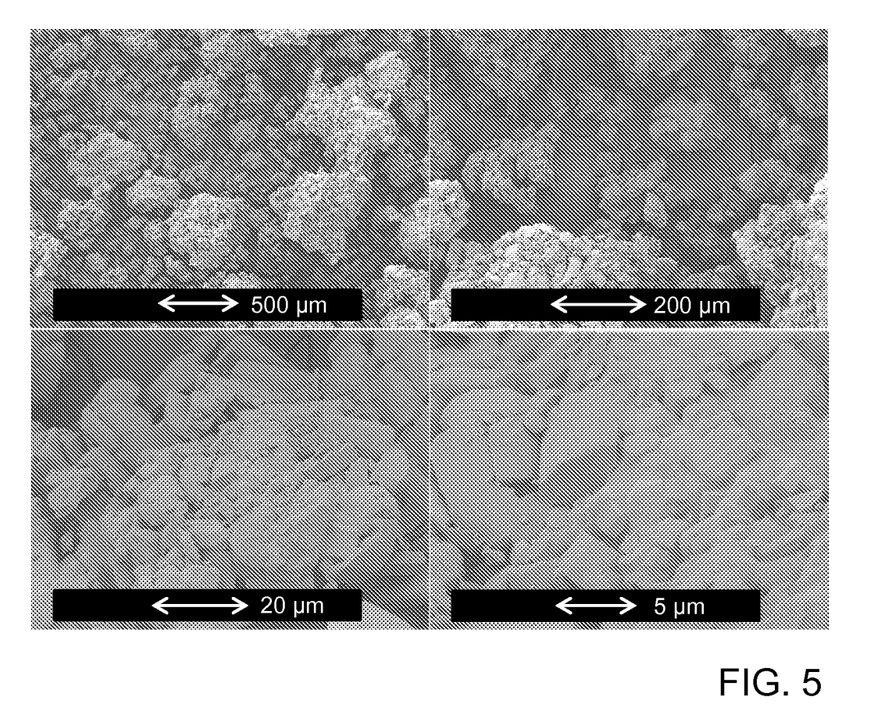
FIG. 5 is a set of SEM images (at different magnifications) of dried, co-processed particles processed according to one embodiment of the disclosure.

FIG. 5 is a set of SEM images (at different magnifications) of the agitated dried co-processed metformin HCl particles described above. The surface of each agglomerate is predominantly covered by the metformin HCl crystals, which are the rod-shaped particles. In the image with 5000 times magnification (lower right), there are noticeably smoother areas on the surface of the agglomerates in which the rod-like crystals are partially embedded. Accordingly, the metformin HCl crystals are agglomerated together with the polymer particles, rather than the material being merely a physical blend. Without intending to be bound by theory, the inventors surmise that the desired dissolution profile is achieved with less release modifying polymer as a result of the intimate mixing of the polymer particles with the active pharmaceutical ingredient during co-processing.

Figure 6:
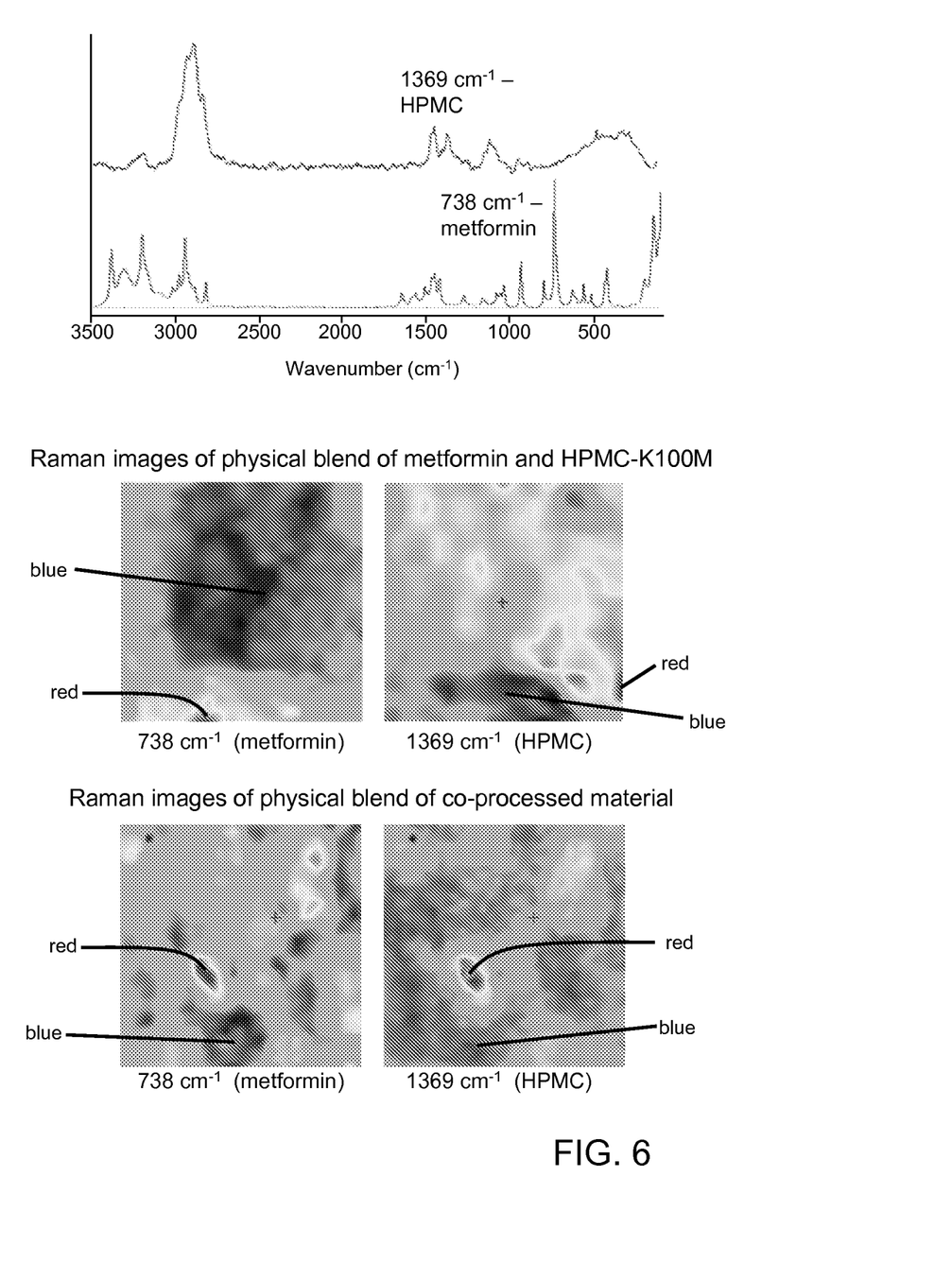
FIG. 6 is (from top to bottom) a Raman spectrum of metformin overlaid with a Raman spectrum of hydroxypropylmethylcellulose; Raman imaging results for a physical blend of metformin HCl and HPMC K100M; and Raman imaging results for a co-processed metformin HCl particles according to one embodiment of the disclosure.

Raman imaging experiments provide additional evidence for the intimate mixing between the polymer and active pharmaceutical ingredient particles. The Raman spectra for HPMC K100M and metformin HCl individually are shown in the top portion of FIG. 6. The characteristic peaks for HPMC K100M and metformin HCl are selected as 738 cm$^{-1}$ and 1369 cm$^{-1}$, respectively. The Raman images from mere physical blends of metformin HCl and HPMC K100M (center portion of FIG. 6) show that when the metformin distribution is high (as indicated by red, yellow and green; in the grayscale images of FIG. 6, red regions are marked as such and yellow and green regions are lighter gray than red and blue regions), the HPMC distribution is low (as indicated by blue; in the grayscale images of FIG. 6, blue regions are marked as such). Similarly, when the HPMC distribution is high, the metformin distribution is low. Accordingly, there is little, if any, spatial correlation between metformin HCl and polymer in the physically blended powders. In contrast to the physically blended powders, co-processed metformin agglomerates (bottom portion of FIG. 6) display essentially the same spatial distribution, indicating that metformin and polymer occupy the same location, suggesting that they are "embedded" in each other. Moreover, there is no peak position shift observed, indicating that there is not substantial interaction at a molecular level during co-processing. Without intending to be bound by theory, the inventors surmise that it is this intimate mixing that enables a lower amount of release modifying polymer to be used to achieve the desired dissolution profile.

Figure 7:
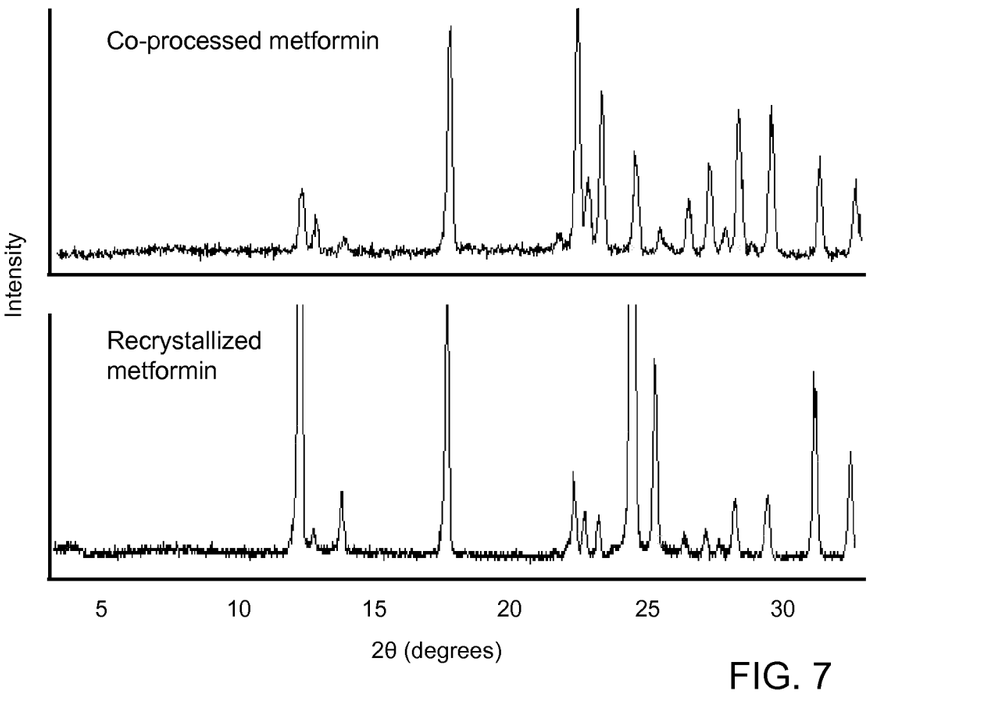
FIG. 7 is a pair of powder x-ray diffraction graphs of co-processed metformin HCl particles according to one embodiment of the disclosure (top); and recrystallized metformin HCl (bottom)

FIG. 7 is a pair of powder x-ray diffraction graphs of co-processed metformin HCl particles according to one embodiment of the disclosure (top); and recrystallized metformin HCl (bottom). Notably, the polymorphic form of the co-processed metformin HCl appears similar to that of the recrystallized commercial material.

As described above, the methods of the disclosure can result in a co-processed particulate material having a relatively high density. For example, the bulk density of 0.35-0.39 g/mL is suitable for direct compression of the co-processed particulate material into a tablet. Shear cell measurements, provided in Table 2, show that the both tray dried and agitated dried co-processed samples display similar or better flow compared to the granules generated by the commercial wet-granulation method, demonstrating the material to be suitable for direct compression. Accordingly, one advantage of the methods described herein is that it can reduce manufacturing cycle time, as the co-processing methods of this disclosure can take less time as compared to current wet granulation methods.

TABLE 2

| Metformin BMS-207150 DP sample | Effective Angle of Internal Friction (°) | Uniaxial Compressive Strength* | Relative Flowability Index |
|---|---|---|---|
| Commercial RX Wet Granulation | 30.8 | 1470 | 2.14 |
| Co-processed Tray Dried** | 32.2 | 1183 | 2.92 |
| Co-processed Agitated Dried | 31.2 | 960 | 3.51 |

*Single point measurement under 3 kPa preconsolidation stress
**Co-processed metformin contains 80:16:4 API:HPMC K100M:NaCMC The strength of the co-processed particles can be evaluated by Granule Integrity Testing (GIT). In this method, material is sieved through 300, 600 and 1000 micron screens. The weight percentage of particles in each size range is determined. Next, the material is dispersed by low-frequency, high intensity acoustic energy (36G and 73G) for 3 minutes, which creates a uniform shear field throughout the entire mixing vessel. After application of the shear field, the sieve analysis is repeated to determine the weight fraction of particles in each size range post-shear. The GIT index is calculated by taking the difference between the weight fractions of particles in each size range before and after the exposure to high intensity energy, and dividing by the weight fraction in that size range before exposure. A GIT index of 0 indicates complete integrity of granules, a GIT index <0.3 indicates robust granules, a GIT index >0.6 indicates fragile granules, and a GIT index of 1 indicates no granule integrity. The results for the co-processed metformin HCl particles described above are provided in Table 3. The GIT indices for both agitated dried and tray dried co-processed material are found to be <0.3 or close to 0, which confirms that the co-processed particles are robust, lowering the risk of attrition during the downstream handling. Accordingly, another advantage of the methods of this disclosure is that they can inhibit segregation of the active pharmaceutical ingredient particles from the polymer material(s).

TABLE 3

| | \>1 mm | 600-1000 μm | 300-600 μm | <300 μm |
|---|---|---|---|---|
| | Granule size fraction | | | |
| Initial weight (%) WG Commercial XR | 0.067 | 9.176 | 22.91 | 67.85 |
| After 36 G (%) | 0.067 | 8.272 | 22.75 | 68.91 |
| Initial weight (%) WG Commercial XR | 0.067 | 7.49 | 22.59 | 69.95 |
| After 73 G (%) | 0.067 | 6.61 | 21.93 | 71.39 |
| Initial weight (%) Co-processed Tray Dried* | 0 | 0.13 | 32.82 | 67.07 |
| After 36 G (%) | 0 | 0.26 | 28.49 | 71.25 |
| Initial weight (%) Co-processed Tray Dried* | 0 | 0.133 | 31.00 | 68.86 |
| After 73 G (%) | 0 | 0.19 | 25.63 | 74.24 |
| Initial weight (%) Co-processed Agitated Dried* | 0 | 4.5 | 57.28 | 38.21 |
| After 36 G (%) | 0 | 4.446 | 58.34 | 37.2 |
| Initial weight (%) Co-processed Agitated Dried* | 0 | 6.4 | 61.2 | 32.4 |
| After 72 G (%) | 0 | 4.4 | 59.29 | 36.29 |

| Metformin DP | 35G | 73G |
|---|---|---|
| | GIT Index | |
| Commercial XR (WG) Initial weight (%) | 0 | 0.029 |
| Co-processed Tray Dried* | 0.132 | 0.173 |
| Initial weight (%) Co-processed Agitated Dried* | 0 | 0.030 |

**Co-processed metformin contains 80:16:4 API:HPMC K100M:NaCMC

Figure 8:
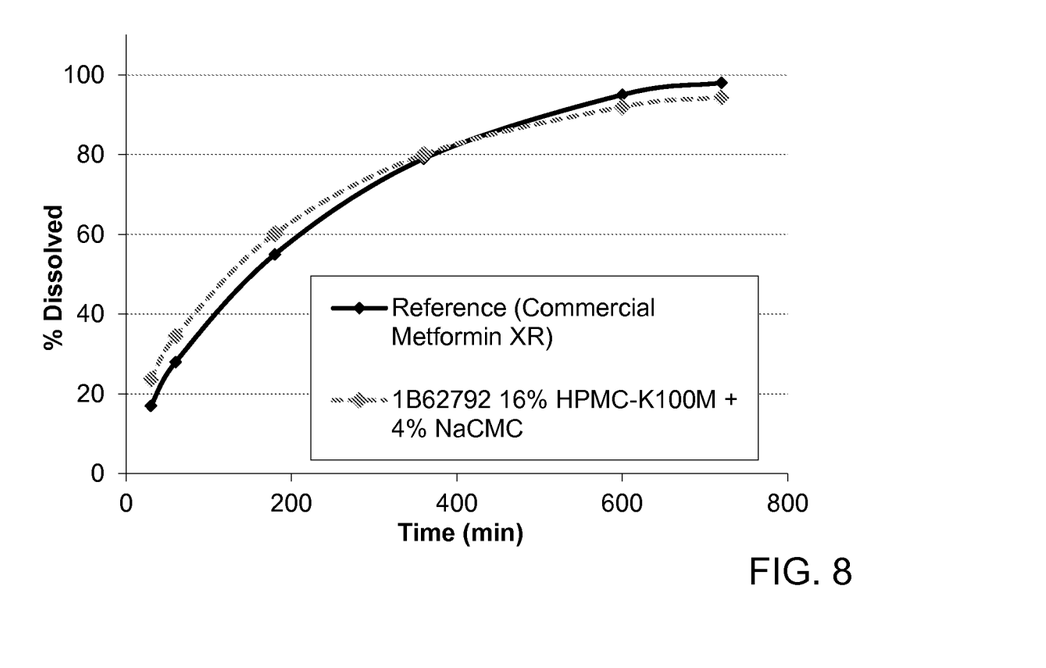
FIG. 8 is a graph of a dissolution profile of a tablet according to one embodiment of the disclosure.

The co-processing method of the disclosure was successfully implemented as described above at 2.5 kg scale with agitated drying to form co-processed metformin HCl particles. The co-processed material had bulk density of 0.36 g/mL, tapped density of 0.42 g/mL and particle size D90 of 1065 μm. 0.5 wt % magnesium stearate was added to the co-processed particles, and the mixture was tableted using direct compression with a single hopper and compression station. The tablet weight for 1000 mg strength was 1250 mg. The co-processed material was very compressible and achieved more than 40 SCU tablet hardness. This formulation prototype exhibited dissolution profile similar to a commercial 1000 mg metformin HCl XR product, as shown in FIG. 8.

Bilayer tablets were also formed from the mixture using two hoppers and two compression stations in a Piccola tablet press. The first layer was formed using the mixture described above, with a weight of 1000 mg metformin HCl. The second layer was a 5 mg dapagliflozin layer, having the composition of Table 4:

TABLE 4

| Component | % w/w per layer | Amount per layer (mg) |
|---|---|---|
| Dapagliflozin | 1.67 | 5.00 |
| Lactose anhydrous | 16.00 | 48.00 |
| Microcrystalline cellulose | 75.83 | 227.50 |
| Crospovidone | 4.00 | 12.00 |
| Silicon dioxide | 1.50 | 4.50 |
| Magnesium stearate | 1.00 | 3.00 |
| Total | 100.00 | 300.00 |

The characteristics of the tablet are provided below:
  Tablet weight: 1559.3 mg (+/−1.5% RSD). This weight is smaller than those of the Glucophage XR formulation (1684 mg) and the reduced mass dapa-Met XR formulation (1580 mg)
  Hardness: 53.0 SCU (layers did not laminate during hardness test)
  Friability: 100 drops=0.01%, 200 drops=0.06%, 400 drops=0.22%
  Delamination test on humidity: 25° C./75% relative humidity and 30° C./65% relative humidity open bottle conditions for seven days-no hairline imperfections/delamination at the layer interface.

Another aspect of the disclosure is a pharmaceutical formulation made by any method described herein.

Another aspect of the disclosure is a pharmaceutical formulation including a water-soluble active pharmaceutical ingredient and one or more release-modifying polymers and optionally one or more binders. The pharmaceutical formulation includes a particulate phase (i.e., either a compressed particulate phase or a plurality of particles) in which the concentration of the active pharmaceutical ingredient (e.g., a metformin salt such as metformin HCl) is in the range of about 60 wt % to about 95 wt % (for example, in the range of about 72 wt % to about 88 wt %). In certain such embodiments, the concentration of the active pharmaceutical ingredient in the particulate phase (e.g., a metformin salt such as metformin HCl) is in the range of about 75 wt % to about 88 wt %. In certain such embodiments, the total concentration of the one or more release-modifying polymers and, if present, the one or more binders is in the range of about 5 wt % to about 40 wt % (for example, in the range of about 5 wt % to about 28 wt %).

In certain embodiments, the one or more release-modifying polymers (for example, hydroxypropylmethylcellulose) are present in an amount in the range of about 5 wt % to about 40 wt % (for example, in the range of about 5 wt % to about 28 wt %, or in an amount in the range of about 10 wt % to about 25 wt %); and optionally one or more binders (e.g., NaCMC, hydroxypropylcellulose) present in an amount up to about 15 wt % (for example, in an amount up to about 8 wt %).

In certain embodiments, any additional excipients are present in the particle phase in an amount up to 10%, up to 5%, or up to 2%. For example, one or more lubricants, glidants or anti-adherents such as magnesium stearate, calcium stearate, stearic acid, oil (e.g., vegetable or mineral), talc or silicon dioxide can be included in the compressed phase. In certain embodiments, the only additional excipients present in the particulate phase are one or more lubricants, glidants or anti-adherents.

The pharmaceutical formulations described herein can for example, be in particulate form (e.g., as dried, co-processed particles as described above). The particles can, for example, be provided as a first particulate phase (e.g., as described above) in a capsule. The pharmaceutical formulation can further include a second particulate phase of other particles, for example, other particles containing one or more other active pharmaceutical agents. For the purposes of the present disclosure, the first particulate phase is distinct from the second particulate phase, even though they may be mixed together. The person of skill in the art would be able to distinguish particles of the first particulate phase from the particles of the second particulate phase, even in such an admixed state.

In another embodiment, the pharmaceutical formulation is a tablet, formed by compression of particles (e.g., the dried, co-processed particles as described above). The tablet can be, for example, formed as a single tablet layer from a single compressed particulate phase, or can be a multilayer tablet (e.g., a bilayer tablet) having multiple compressed particulate phases. For example, in one embodiment, the tablet includes a compressed particulate phase as described herein as a first tablet layer; and a second tablet layer adjacent the first tablet layer, the second tablet layer including a second active pharmaceutical agent (e.g., dapagliflozin).

Tablets can be coated with one or more coatings surrounding the first tablet layer (and any other tablet layers present), as the person of skill in the art would appreciate. One or more of the coatings can include an active pharmaceutical agent. For example, in one embodiment, a first tablet layer formed from a compressed particulate phase as described herein is coated with a coating that includes saxagliptin or a pharmaceutically acceptable salt thereof. Such coatings are described, for example, in U.S. Pat. No. 7,951,400, which is hereby incorporated herein by reference in its entirety.

In certain embodiments of the pharmaceutical dosage forms (e.g., tablets or capsules) described herein, the amount of the active pharmaceutical ingredient is at least about 500 mg, or even at least about 1000 mg. For example, in certain embodiments, the amount of the active pharmaceutical ingredient is in the range of about 500 mg to about 2000 mg. Such pharmaceutical formulations can, for example, be prepared using the methods of the present disclosure.

Further, the foregoing description of embodiments has been presented for the purposes of illustration and description. It is not intended to be exhaustive or to limit the disclosure to the precise forms disclosed. As the person of skill in the art will recognize, many modifications and variations are possible in light of the above teaching. It will be apparent to those skilled in the art that various modifications and variations can be made without departing from the scope of the disclosure. Thus, it is intended that the present disclosure cover the modifications and variations of this disclosure provided they come within the scope of the claims and their equivalents.

What is claimed is:

1. A method for making co-processed particles, the co-processed particles comprising a water-soluble active pharmaceutical ingredient and one or more release-modifying polymers and optionally one or more binders, the method comprising
   providing an agitated suspension or slurry of the one or more release-modifying polymers and, if present, the one or more binders, in one or more organic solvents, the one or more organic solvents being at least partially water-miscible, one or more of the organic solvents being ethyl acetate, isopropyl acetate, or butyl acetate, wherein
      the one or more organic solvents together are an antisolvent for the active pharmaceutical ingredient, and
      the one or more release-modifying polymers and, if present, the one or more binders, are not dissolved in the one or more organic solvents;
   adding an aqueous solution of the active pharmaceutical ingredient to the agitated suspension or slurry, water being sufficiently miscible with the one or more organic solvents such that the water added as part of the aqueous solution forms a single liquid phase with the one or more organic solvents of the suspension or slurry, the addition thereby precipitating the active pharmaceutical ingredient, wherein
      less than 5% of the one or more release-modifying polymers and, if present, the one or more binders, are dissolved in the liquid phase of the suspension or slurry upon the addition, and
      at least about 80% of the active pharmaceutical ingredient is precipitated upon the addition;
   separating the active pharmaceutical ingredient, the one or more release-modifying polymers, and, if present, the one or more binders from the liquid phase yield co-processed particles that comprise agglomerates of precipitate particles of the active pharmaceutical ingredient with the one or more release-modifying polymers and, if present, the one or more binders; and
   drying the co-processed particles.

2. The method according to claim 1, further comprising compressing the dried co-processed particles to form one or more tablets.

3. The method according to claim 2, wherein the dried co-processed particles are compressed with a plurality of second particles to form a multilayer tablet.

4. The method according to claim 1, further comprising filling the dried co-processed particles in one or more capsules to form one or more capsule dosage forms.

5. The method according to claim 1, wherein the one or more organic solvents are acetone and ethyl acetate.

6. The method according to claim 1, wherein the active pharmaceutical agent is metformin or a pharmaceutically acceptable salt thereof.

7. The method according to claim 6, wherein the active pharmaceutical agent is metformin HCl.

8. The method according to claim 7, wherein the release modifying polymer is hydroxypropylmethylcellulose.

9. The method according to claim 8, wherein the agitated suspension or slurry includes the one or more binders.

10. The method according to claim 8, wherein the binder is carboxymethylcellulose or hydroxypropylcellulose.

11. The method according to claim 1, wherein the agitated suspension or slurry includes no binder, and the co-processed particles include no binder.

12. The method according to claim 1, wherein the separation is performed by filtration.

13. The method according to claim 1, wherein the co-processed particles are not completely deliquored during the separation.

14. The method according to claim 1, further comprising, before drying the separated co-processed particles, washing the co-processed particles with a water-miscible solvent.

15. The method according to claim 14, wherein the water miscible solvent includes water in an amount in the range of about 1 wt % to about 10 wt %.

16. The method according to claim 1, wherein the drying is performed with agitation.

17. The method according to claim 2, further comprising providing a coating surrounding each of the one or more tablets, the coating comprising a second active pharmaceutical agent.

18. The method according to claim 17, wherein the second active pharmaceutical agent is saxagliptin or a pharmaceutically acceptable salt thereof.

19. The method according to claim 1, wherein the dried co-processed particles comprise the water-soluble active pharmaceutical ingredient in an amount in the range of about 60 wt % to about 95 wt %; and the one or more release-modifying polymers and optionally one or more binders in a total amount in the range of about 5 wt % to about 40 wt %.

20. The method according to claim 19, wherein the dried co-processed particles comprise the one or more release-modifying polymers in an amount in the range of about 5 wt % to about 40 wt %, and optionally the one or more binders in an amount up to about 15 wt %.

21. The method according to claim 19, wherein any additional excipients are present in the particulate phase in an amount up to about 10 wt %.

22. The method according to claim 19, wherein the only additional excipients in the particulate phase are one or more lubricants, glidants or anti-adherents.

23. The method according to claim 19, further comprising compressing the dried co-processed particles to form one or more tablets.

24. The method according to claim 23, further comprising providing a coating surrounding each tablet, the coating including an active pharmaceutical agent.

25. The method according to claim 23, wherein the amount of water-soluble active pharmaceutical ingredient in each tablet is in the range of about 500 mg to about 2000 mg.

26. The method according to claim 1, wherein the active pharmaceutical ingredient crystallizes in the suspension or slurry upon addition.

27. The method according to claim 1, wherein after the addition less than 2% of polymer material in the suspension or slurry is dissolved.

28. The method according to claim 1, wherein at least about 90% of the active pharmaceutical ingredient precipitates upon the addition.

29. A method for making co-processed particles, the co-processed particles comprising a water-soluble active pharmaceutical ingredient and one or more release-modifying polymers and optionally one or more binders, the method comprising
providing an aqueous solution of the active pharmaceutical ingredient;
providing a suspension or slurry of the one or more release-modifying polymers and optionally the one or more binders, in one or more organic solvents,
wherein the one or more organic solvents together are an antisolvent for the active pharmaceutical ingredient and are at least partially water-miscible, one or more of the organic solvents being ethyl acetate, isopropyl acetate, or butyl acetate;
precipitating the active pharmaceutical ingredient in the suspension or slurry by adding the aqueous solution of the active pharmaceutical ingredient to the suspension or slurry while agitating the suspension or slurry,
wherein less than 5% of the one or more release-modifying polymers and, if present, the one or more binders are dissolved in the liquid phase of the suspension or slurry upon the addition,
wherein water is sufficiently miscible with the one or more organic solvents such that the water added as part of the aqueous solution forms a single liquid phase with the one or more organic solvents of the suspension or slurry, and
wherein the addition precipitates at least about 80% of the active pharmaceutical ingredient;
separating the active pharmaceutical ingredient, the one or more release-modifying polymers, and, if present, the one or more binders from the one or more organic solvents to yield co-processed particles that comprise agglomerates of precipitate particles of the active pharmaceutical ingredient with particles of the one or more release-modifying polymers and, if present, of the one or more binders; and
drying the co-processed particles.

* * * * *